US011511017B2

(12) United States Patent
Shepard et al.

(10) Patent No.: US 11,511,017 B2
(45) Date of Patent: *Nov. 29, 2022

(54) LIGAMENT RECONSTRUCTION

(71) Applicant: ARTHREX, INC., Naples, FL (US)

(72) Inventors: David O. Shepard, Naples, FL (US); Robert Harrison, Naples, FL (US); Robert Benedict, Naples, FL (US)

(73) Assignee: ARTHREX, INC., Naples, FL (US)

( * ) Notice: Subject to any disclaimer, the term of this patent is extended or adjusted under 35 U.S.C. 154(b) by 370 days.

This patent is subject to a terminal disclaimer.

(21) Appl. No.: 16/815,228

(22) Filed: Mar. 11, 2020

(65) Prior Publication Data
US 2020/0289707 A1 Sep. 17, 2020

Related U.S. Application Data

(60) Provisional application No. 62/817,107, filed on Mar. 12, 2019.

(51) Int. Cl.
A61L 27/36 (2006.01)

(52) U.S. Cl.
CPC ....... A61L 27/3662 (2013.01); A61L 27/3608 (2013.01); A61L 27/3616 (2013.01); A61L 27/3687 (2013.01); A61L 2400/18 (2013.01); A61L 2430/10 (2013.01)

(58) Field of Classification Search
None
See application file for complete search history.

(56) References Cited

U.S. PATENT DOCUMENTS

| 4,894,063 | A | 1/1990 | Nashef |
| 5,612,028 | A | 3/1997 | Sackier et al. |
| 5,723,010 | A | 3/1998 | Yui |
| 6,152,142 | A | 11/2000 | Tseng |
| 6,264,600 | B1 | 7/2001 | Grimm |
| 6,326,019 | B1 | 12/2001 | Tseng |
| 7,322,928 | B2 | 1/2008 | Reed et al. |
| 7,771,442 | B2 | 8/2010 | Shriver |
| 7,914,779 | B2 | 3/2011 | Hariri |
| 8,105,634 | B2 | 1/2012 | Liu et al. |
| 8,257,393 | B2 | 9/2012 | Cichocki |
| 8,318,197 | B2 | 11/2012 | Steed et al. |
| 8,529,888 | B2 | 9/2013 | Meiron et al. |
| 8,840,665 | B2 | 9/2014 | Young et al. |
| 9,139,813 | B2 | 9/2015 | Hariri |
| 9,175,262 | B2 | 11/2015 | Aberman |
| 9,205,177 | B2 | 12/2015 | Schrogi et al. |
| 9,364,585 | B2 | 6/2016 | Takabe |
| 9,486,316 | B2 | 11/2016 | Horton et al. |
| 9,808,492 | B2 | 11/2017 | Broussard |
| 9,943,551 | B2 | 4/2018 | Koob et al. |
| 10,004,605 | B2 | 6/2018 | Grotz |
| 10,271,942 | B2 | 4/2019 | Tokish et al. |
| 10,314,688 | B2 | 6/2019 | Shepard et al. |
| 2003/0187515 | A1 | 10/2003 | Hariri et al. |
| 2004/0048796 | A1 | 3/2004 | Hariri et al. |
| 2006/0085003 | A1* | 4/2006 | Schmieding .......... A61L 27/227 604/500 |
| 2007/0048292 | A1 | 3/2007 | Morita et al. |
| 2007/0292401 | A1 | 12/2007 | Harmon et al. |
| 2010/0069925 | A1 | 3/2010 | Friedman et al. |
| 2011/0152898 | A1 | 6/2011 | Kochevar et al. |
| 2011/0206776 | A1 | 8/2011 | Tom et al. |
| 2011/0212063 | A1 | 9/2011 | Tom et al. |
| 2011/0212064 | A1 | 9/2011 | Jansen et al. |
| 2011/0212065 | A1 | 9/2011 | Jansen et al. |
| 2011/0280845 | A1 | 11/2011 | Edinger et al. |
| 2011/0307059 | A1 | 12/2011 | Young et al. |
| 2012/0010708 | A1 | 1/2012 | Young et al. |
| 2012/0010727 | A1 | 1/2012 | Young et al. |
| 2012/0114712 | A1 | 5/2012 | Liu et al. |
| 2012/0141595 | A1 | 6/2012 | Tseng et al. |
| 2013/0073055 | A1 | 3/2013 | Park et al. |
| 2014/0037598 | A1 | 2/2014 | Jansen et al. |
| 2014/0052247 | A1 | 2/2014 | Daniel et al. |
| 2014/0067058 | A1 | 3/2014 | Koob et al. |
| 2014/0127317 | A1 | 5/2014 | Jansen et al. |
| 2014/0140966 | A1 | 5/2014 | Tom et al. |
| 2014/0186461 | A1 | 7/2014 | Broussard |
| 2014/0255508 | A1 | 9/2014 | Morse et al. |
| 2014/0257500 | A1 | 9/2014 | Grotz |
| 2014/0271776 | A1 | 9/2014 | Vines et al. |
| 2014/0343688 | A1 | 11/2014 | Morse et al. |
| 2015/0010506 | A1 | 1/2015 | Jansen et al. |
| 2015/0190433 | A1 | 7/2015 | Edinger et al. |
| 2015/0216910 | A1 | 8/2015 | Horton et al. |
| 2015/0267170 | A1 | 9/2015 | Hariri |

(Continued)

FOREIGN PATENT DOCUMENTS

| CN | 85108766 A | 7/1986 |
| EP | 0637452 A1 | 2/1995 |

(Continued)

OTHER PUBLICATIONS

Woodall, Brittany M; et al; "Anterior Cruciate Ligament Reconstruction With Amnion Biological Augmentation" Arthroscopy Techniques, 7, e355-e360, 2018 (Year: 2018).*
Schulze-Tanzil, G; et al; "Cultivation of human tenocytes in high-density culture" Histochemistry and Cell Biology, 122, 219-228, 2004 (Year: 2004).*
Arthrex Amnion Matrix data Sheet, Arthrex, 2021 (Year: 2021).*
Choi et al, "Full-Thickness Skin Wound Healing Using Human Placenta-Derived Extracellular Matrix Containing Bioactive Molecules", Tissue Engineering: Part A, 19(3-4):329-339, (2013).
Koob et al, "Properties of dehydrated human amnion/chorion composite grafts: Implications for wound repair and soft tissue regeneration", J Biomed Mater Res, Part B, 2014:102B:1353-1362, (2014).

(Continued)

Primary Examiner — David W Berke-Schlessel
(74) Attorney, Agent, or Firm — DLA Piper LLP US

(57) ABSTRACT

The present disclosure describes methods of treating a ligament injury with ligament grafting.

20 Claims, No Drawings

(56) References Cited

U.S. PATENT DOCUMENTS

| | | |
|---|---|---|
| 2015/0328264 A1 | 11/2015 | Lucey et al. |
| 2016/0000970 A1 | 1/2016 | Rosines |
| 2016/0058799 A1 | 3/2016 | Aberman |
| 2016/0206778 A1 | 7/2016 | Park et al. |
| 2016/0220618 A1 | 8/2016 | Takebe |
| 2016/0249932 A1 | 9/2016 | Rogers et al. |
| 2016/0263281 A1 | 9/2016 | Koob et al. |
| 2016/0303171 A1 | 10/2016 | Tseng et al. |
| 2016/0303290 A1 | 10/2016 | Morse et al. |
| 2016/9028775 | 10/2016 | Britt |
| 2017/0258965 A1 | 9/2017 | Reichmann et al. |
| 2018/0214493 A1 | 8/2018 | Koob et al. |
| 2018/0221418 A1 | 8/2018 | Daniel et al. |
| 2018/0250440 A1 | 9/2018 | Daniel et al. |
| 2018/0280572 A1 | 10/2018 | Daniel et al. |
| 2018/0344892 A1 | 12/2018 | Cotton et al. |
| 2018/0353651 A1 | 12/2018 | Reid et al. |
| 2018/0360886 A1 | 12/2018 | Tom et al. |

FOREIGN PATENT DOCUMENTS

| | | |
|---|---|---|
| EP | 0734736 A1 | 10/1996 |
| EP | 1036865 A1 | 9/2000 |
| WO | 199837903 A1 | 9/1998 |
| WO | 2003082201 A1 | 10/2003 |
| WO | 2011064669 A2 | 6/2011 |
| WO | 2011103446 A1 | 8/2011 |
| WO | 2011103451 A1 | 8/2011 |
| WO | 2011103455 A1 | 8/2011 |
| WO | 2011103462 A1 | 8/2011 |
| WO | 2012112410 A2 | 8/2012 |
| WO | 2012112441 A1 | 8/2012 |
| WO | 2013049052 A2 | 4/2013 |
| WO | 2013130547 A1 | 9/2013 |
| WO | 2014028325 A1 | 2/2014 |
| WO | 2014028326 A1 | 2/2014 |
| WO | 2014028327 A1 | 2/2014 |
| WO | 2014028657 A1 | 2/2014 |
| WO | 2014143990 A1 | 9/2014 |
| WO | 2014160124 A1 | 10/2014 |
| WO | 2015004609 A1 | 1/2015 |
| WO | 2015120405 A1 | 8/2015 |
| WO | 2015134936 A1 | 9/2015 |
| WO | 2015171142 A1 | 11/2015 |
| WO | 2015171143 A1 | 11/2015 |
| WO | 2015171144 A1 | 11/2015 |
| WO | 2016015754 A1 | 2/2016 |
| WO | 2016128916 A1 | 8/2016 |
| WO | 2016196313 A1 | 12/2016 |
| WO | 2017049210 A1 | 3/2017 |
| WO | 2017049215 A1 | 3/2017 |
| WO | 2017112934 A1 | 6/2017 |
| WO | 2017140914 A1 | 8/2017 |
| WO | 2018231726 A1 | 12/2018 |

OTHER PUBLICATIONS

Seo et al, "Co-effect of silk and amniotic membrane for tendon repair", Journal of Biomaterials Science, Polymer Edition, 27(12):1232-1247, (2016).

Abousleiman et al, "The Human Umbilical Vein: A Novel Scaffold for Musculoskeletal Soft Tissue Regeneration", Artificial Organs, 32(9):735-741, (2016).

* cited by examiner

LIGAMENT RECONSTRUCTION

CROSS-REFERENCE TO RELATED APPLICATIONS

This application claims the benefit of Provisional U.S. Application No. 62/817,107 filed Mar. 12, 2019, which is hereby incorporated by reference in its entirety.

BACKGROUND

This disclosure relates to ligament reconstruction procedures.

DETAILED DESCRIPTION

Placental tissue can be used in the augmentation of repair, reconstruction, and regeneration of patient musculoskeletal tissue injury due to the natural components of the placental tissue as well as the lack of antigens.

Placental tissue can be used for the treatment of musculoskeletal tissue injuries and degenerative conditions in a patient. Tissues that can be treated, repaired, regenerated, and/or restored include, for example, ligaments, joints, connective tissue, cartilage, intervertebral disk, bone, anterior cruciate ligament, posterior cruciate ligament, medial collateral ligament, lateral collateral ligament, popliteofibular ligament, posterolateral corner, patellar tendon, quadriceps tendon, medial or lateral meniscus, medial or lateral patellofemoral ligament, anterolateral ligament, rotator cuff tendon, glenoid labrum, subscapularis tendon, biceps tendon, coracoclavicular ligaments, anterior talofibular ligament, calcaneofibular ligament, spring ligament, posterior tibialis, anterior tibialis, tendon grafts, extensor and flexor tendons of the hand, foot, upper and lower extremities, intervertebral disk material, damaged or torn muscle tissue including but not limited to, the hamstring muscles, quadriceps, gastrocnemius, soleus, adductors, abductors, hip external and internal rotators, flexors, wrist, elbow and hand extensors, flexors, and other tendons and muscles throughout the musculoskeletal system. A musculoskeletal tissue injury or degeneration can be, for example, a connective tissue injury or degeneration, cartilaginous tissue injury or degeneration, fibrous tissue injury or degeneration, muscle tissue injury or degeneration, or skeletal tissue injury or degeneration.

Placental tissue, optionally in conjunction with mesh constructs or sutures, can be incorporated into a primary tissue repair, allograft reconstruction, autograft reconstruction, engineered tissue scaffold reconstruction, or in regenerative applications thereby producing a tissue hybrid. A tissue hybrid can provide a bio-inductive scaffold for use in tissue repair (tendinopathies of the shoulder, knee, elbow, and ankle, for example). In reconstruction procedures, the vascularity of a tissue may be compromised, particularly in a tissue's inner-substance (e.g., an ACL reconstruction). A tissue hybrid or placental tissue, as described herein, can augment healing, incorporation, or regeneration of a damaged tissue over a non-hybrid primary tissue repair or allograft/autograft or engineered tissue scaffold.

Placental tissue (e.g., tissue hybrid, placental tissue streamer, placental tissue patch hybrid, suture placental tissue hybrid, engineered scaffold placental tissue hybrid) can be incorporated into an injured or degenerative tissue for the augmentation of healing the damaged tissue, where the damage to the tissue is not severe enough to warrant structural surgical repair. Examples of such tissue damage not requiring formal surgical structural repair including, for example, rotator cuff tendinopathy, partial thickness tear of tissue, patellar tendinitis, lateral epicondylitis, medial meniscal degeneration, degenerative disk disease, or the like.

In an embodiment, degenerative tissues that are not necessarily in need of structural repair are treated. For example, rotator cuff tendinosis, rotator cuff partial thickness tears, degenerative meniscal tears, Achilles tendinopathy, lateral epicondylitis, patellar tendinopathy, and degenerative disk disease can be treated by injecting and/or inserting or augmenting the midsubstance with a placental streamer to augment healing without the need for a formal structural surgical repair. Degenerative tissues can also be treated by contacting or wrapping the suture placental tissue hybrids, engineered scaffold placental tissue hybrid, or placental tissue patch hybrids with or around the degenerated tissues.

Degenerative tissue may be partially torn but not structurally compromised. The placement of placental tissue streamers, tissue hybrids, placental tissue patch hybrids, and suture placental tissue hybrids in this case is intended to augment healing, repair, and/or regeneration of the damaged or degenerative tissue. Examples of this application include but are not limited to, tendinosis, partial thickness tendon tears, degenerative disk disease or annular tears, degenerative meniscal tears, degenerative labral tears, partial thickness ligament tears, muscle injury, ligament sprains, and atrophic/fatty infiltrated muscle such as rotator cuff muscle damaged with Goutallier stages 1-4 muscle atrophy/fatty infiltration.

Tissue Hybrids

In embodiments of the present disclosure, a tissue hybrid is created by threading a placental tissue streamer through a midsubstance of a tissue or engineered tissue scaffold, placing a placental tissue streamer along the tissue or engineered tissue scaffold, or wrapping the tissue or engineered tissue scaffold with a placental tissue streamer. Other tissue hybrids include placental tissue hybrids, engineered tissue placental tissue hybrids, suture placental tissue hybrids, and placental tissue patch hybrids, which can be threaded through a midsubstance of a tissue or engineered tissue scaffold, placed alongside a tissue or engineered tissue scaffold, anchored or attached to a tissue or engineered tissue scaffold, or wrapped around a tissue or engineered tissue scaffold. In an embodiment, the tissue is healthy tissue. In an embodiment, the tissue is damaged or degenerated tissue. In an embodiment, the tissue is healthy graft tissue or an engineered tissue scaffold. The midsubstance of the tissue refers to the longitudinal inside of the tissue or engineered tissue scaffold.

A tissue of a tissue hybrid can be autograft, allograft, xenograft, engineered tissue scaffold, or combinations of the like. Xenograft materials can be obtained from mammalian sources, including, but not limited to, equine, canine, feline, bovine, porcine, sheep, or goat, and human sources.

Placement

In an embodiment, at least one placental tissue streamer is threaded through a damaged tissue or engineered tissue scaffold, creating a tissue hybrid. In an embodiment, a tissue hybrid comprises one or more amniotic membrane streamers and a damaged tissue, where the streamer is located in the midsubstance of the damaged tissue or within the damaged tissue. In an embodiment one or more placental tissue streamers (including placental tissue streamer ropes and placental tissue streamer stacks) are placed alongside or in contact with the tissue to be treated. In this case, the one or more placental streamers can optionally be attached to the tissue to be treated via, for example, one or more sutures. In an embodiment, the tissue of the tissue hybrid is damaged tissue. In an embodiment, the tissue of the tissue hybrid is healthy tissue. In an embodiment, the midsubstance comprises a midpoint, which refers to the intermediate or longitudinally central part of the tissue. The midsubstance does not have to be the exact center of the tissue. In an embodiment, a placental tissue streamer can be run through the midsubstance, adjacent to the midpoint of the tissue. The streamer can be threaded through the tissue so as to run along the length of the tissue. In another embodiment, at least one streamer is threaded through a tissue graft (e.g., an allograft, autograft, or xenograft) or engineered tissue scaffold that will be used to repair reconstruct or regenerate the injured soft tissue of the patient. In this embodiment, the tissue hybrid comprises a placental tissue streamer and a healthy tissue graft, allograft, autograft, or xenograft, where the streamer is threaded through the midsubstance of the tissue graft. A placental tissue streamer can also be placed alongside, on the top of, on the bottom of, or wrapped around a tissue (healthy, damaged, degenerated, or graft tissue) or engineered tissue scaffold.

Streamer and Streamer Placement

A placental tissue streamer can be attached to damaged, injured tissue, degenerated tissue, or healthy graft tissue of a tissue hybrid or to a placental tissue streamer attachment site. A placental tissue streamer can also be attached to an engineered tissue scaffold. When a streamer is attached to a placental tissue streamer attachment site, the streamer is located within healthy tissue of the patient in the proximity of the injury or damage. A streamer attachment site can be located in muscle, tendon, ligament, joint, connective tissue, cartilage, bone, intervertebral disk, or the like. A placental tissue streamer attachment site can be located in the tissue hybrid. In an embodiment, the placental tissue streamer comprises two ends, where one end of the placental tissue streamer can be attached to a placental tissue streamer attachment site; the second end of the placental tissue streamer can be attached to a different placental tissue streamer attachment site. The placental tissue streamer can be attached at a placental tissue streamer attachment site through attachment processes known in the art. An example of such an attachment process is suturing the end of a streamer to the tissue of the tissue hybrid, where the tissue of the tissue hybrid is damaged or injured tissue, healthy graft tissue, an engineered tissue scaffold, or combinations thereof. In an embodiment, a streamer is not attached to damaged or injured tissue, healthy graft tissue, or engineered tissue scaffold; rather, the ends of the streamer and the tissue hybrid are attached independently to the same two healthy tissue attachment sites. In such an embodiment, the healthy tissue attachment site can be located in non-damaged tissue of the patient in proximity to the injury, damaged tissue, or wound. The non-damaged tissue can be muscle, tendon, ligament, connective tissue, joint, cartilage, bone, intervertebral disk, or the like. For example, in an anterior cruciate ligament repair or reconstruction, one end of the patellar tendon can be attached to the femur while the other end is attached to the tibia. In this example, the tissue hybrid, along with the streamer located through the midsubstance of the tissue hybrid can be attached to the bone at the femur and tibia. In such an example, there are two healthy tissue attachment sites, at each end of the patellar tendon graft. Attaching both the streamer and the tissue hybrid at the same attachment site allows for anchoring of both the streamer and the tissue hybrid. Such an attachment is performed by methods known in the art.

In an embodiment, a streamer is threaded through the tissue while the tissue is still attached to the patient at the tissue's natural attachment site. A tissue's natural attachment site is the location where that tissue, if healthy, would be attached to the subject's body. For example, an Achilles tendon that is ruptured between the tissue's natural attachment sites at the calcaneus and gastrocnemius is still attached at its natural attachment sites. The streamer is threaded through the midsubstance of the tissue starting near the tissue's natural attachment site. The streamer is attached to the Achilles tendon through known methods, such as suturing or at the bony insertion through the use of a suture anchor. The streamer runs the length of the Achilles tendon and is attached to the tendon at streamer attachment points near where the Achilles tendon is attached to the calcaneus and gastrocnemius.

In an embodiment one or more placental tissue streamer ropes or placental tissue streamer stacks are contacted with a damaged tissue (e.g., placing the ropes or stacks alongside the damaged tissue). The one or more placental tissue streamer ropes or placental tissue streamer stacks can optionally be attached to the damaged tissue via, for example sutures.

Rotator Cuff

In an embodiment, rotator cuff tendinopathy can be treated with the insertion of an amniotic streamer. Rotator cuff tendinopathy is often not treated initially through surgical means; rather it is usually treated through subacromial steroid injection. However, in the exemplary embodiment, a streamer is inserted into the damaged rotator cuff tissue. This can be done through known surgical means, but also through ultrasound guided injection/insertion. The surgeon can use a needle loaded with a streamer and an ultrasound to guide the needle to the proper location. Then the streamer can be injected/inserted into the tissue.

Placental tissue streamers can also be delivered to other tendinopathies in the patellar tendon, lateral and medial epicondylitis, ankle, Achilles, and to muscle strains and tears such as the hamstring or quadriceps muscles, gastrocnemius muscle, soleus muscle, or other muscle injury or degeneration, as well as sprained ligaments such as around the ankle, knee, elbow, or shoulder.

Anterior Cruciate Ligament (ACL)

In an embodiment, an ACL is treated. A tissue graft, as known in the art, can be used to replace the damaged ACL. The tissue graft can either be a patellar tendon of the patient, the patellar tendon of a cadaver, a hamstring graft of the patient, or a hamstring graft of a cadaver, quadriceps tendon of the patient or cadaver, or other tendon such as the tibialis anterior or posterior of a cadaver. At least one placental tissue streamer can be threaded through the midsubstance of the tissue graft. Once the streamer is threaded through the midsubstance of the tissue graft, the tissue hybrid is formed. The tissue hybrid is then placed in the patient.

In an embodiment, an ACL can be repaired or reconstructed using a tissue graft. The graft is obtained by methods known in the art. A placental tissue streamer can be threaded through the midsubstance of the tissue graft for the length of the tissue graft, forming a tissue hybrid. The placental tissue streamer can be sutured to the tissue graft at each end of the tissue graft. The tissue hybrid can then be administered to the patient and attached at an anchoring site, a site of attachment, located in the subject's femur and an anchoring site in the subject's tibia.

A full tear of a subject's ACL can be repaired or reconstructed with methods described herein. A tissue graft can be used to replace the torn ACL where the tissue graft comprises a midsubstance, a first end, and a second end. A placental tissue streamer can be threaded through the midsubstance of the tissue graft creating a tissue hybrid. The first end of the tissue hybrid can be attached to the subject at an anchoring site on the subject's femur. The second end of the tissue hybrid can be attached to the subject at an anchoring site on the subject's tibia.

One exemplary method is the repair of a human anterior cruciate ligament. A placental tissue streamer can be removed from the site of storage and thawed if the streamer was cryopreserved. The patellar tendon of the patient can be removed through methods known in the art. The amniotic tissue streamer can be threaded through the central portion of the patellar tendon. Once the streamer is threaded through the midsubstance of the patellar tendon, the tissue hybrid is formed. The streamer is not attached to the tissue hybrid. Rather, the tissue hybrid can be placed in the subject and is attached to the two healthy tissue attachment sites, one in the femur and one in the tibia.

In an embodiment, a patient's torn ligament or tendon is recovered (e.g., mechanical excision by a device such as the GraftNet™ collector). Recovered tissue can be particulated, minced, digested, or chopped by mechanical or enzymatic processing such that viable cells remain. This tissue composition can be combined with autologous or allogenic blood fractions (e.g., PRP, BMC, etc.) or other biological material (e.g., human thrombin or an animal source activating agent to cause gelation) for treatments. Administering a tissue composition (e.g., a tendon composition or ligament composition) can be useful in aiding a tendon or ligament graft to heal after placement. Administration of a tissue composition can be injection directly into the graft, injection into the surrounding joint space, or into embodiments of methods disclosed herein where a graft is wrapped in placental tissue. When grafts are wrapped in placental tissue (e.g., amnion, chorion, etc.) and stitched to form water tight compartments, the tissue composition can be injected directly into one or more of these water tight compartments. In an embodiment, a tissue composition can be injected into the water tight compartment followed by an injection of a biological agent (e.g., PRP, BMC, etc.) or other biological material (e.g., human thrombin or an animal source activating agent to cause gelation). In an embodiment, a biological agent or biological material can be injected into the water tight compartment followed by an injection of the tissue composition. Alternatively, the tissue composition and the biological agent or biological material can be mixed together and injected into a water tight compartment as one mixture.

In a specific embodiment, an anterior cruciate ligament is torn. A stump of the ligament remains attached to the tibia. The stump is resected and mechanically processed in a GraftNet™ collector. The ligament particulates are solubilized in a liquid carrier. An ACL reconstruction is performed on a patient wherein the graft is wrapped in amnion. The graft is wrapped in amnion multiple times creating multiple layers. One cerclage stitch is placed at either end of the amnion membrane after wrapping. A running stitch was also placed at the end of the amnion membrane. The two cerclage stitches and the running stitch created multiple water-tight compartments, which can be dependent on the number of layers of wrapping. The water-tight compartments are filled with the ligament composition and a biological agent (e.g., PRP or BMC) or other biological material after implantation of the graft.

Achilles Tendon

In an embodiment, a fully or partially ruptured human Achilles tendon can be repaired. A placental streamer is threaded through the midsubstance of the Achilles tendon starting at the calcaneus end of the tendon. The streamer can be attached to the Achilles tendon near the site of where the Achilles tendon is attached to the calcaneus. The streamer continues to be threaded through the midsubstance for the length of the Achilles tendon until reaching the gastrocnemius. The streamer can then be attached to the Achilles tendon near the site of where the Achilles tendon and the gastrocnemius attach to each other. Where the tendon is avulsed off of the bone, the streamer can be used to attach the damaged tissue to the bone by direct bone attachment via a suture anchor where the placental streamer is either threaded through the anchor eyelet, or placed within a hollow suture that is threaded through the suture anchor eyelet.

For example, an Achilles tendon can comprise a midsubstance, a calcaneous end, and/or a gastrocnemius end where the calcaneous end attaches to the subject's calcaneous, and/or the gastrocnemius end attaches to the subject's gastrocnemius. The subject's damaged Achilles tendon can be the tissue of the tissue hybrid. The placental tissue streamer comprises two ends: a first end and a second end and is threaded through the midsubstance of the damaged Achilles tendon, wherein the first end of the placental tissue streamer is inserted at either the calcaneous end or the gastrocnemius end of the Achilles tendon, and the placental tissue streamer is threaded to the opposite end of the Achilles tendon. One of the two placental tissue streamer ends is attached to an attachment site at the calcaneous end of the Achilles tendon; and the other placental tissue streamer end is attached to an attachment site at the gastrocnemius end of the Achilles tendon.

In an embodiment, a damaged Achilles tendon can be strengthened using multiple placental tissue streamers. The Achilles tendon can be repaired or augmented by methods known in the art or with the use of an augmentative engineered tissue scaffold containing placental tissue streamers. After the repair or augmentation, two or more placental tissue streamers are entwined to form a placental tissue streamer rope. The rope can be threaded through the midsubstance of the Achilles tendon starting at the calcaneus end of the tendon. The rope can be sutured to the Achilles tendon near the site of where the Achilles tendon is attached to the calcaneus. The rope continues to be threaded through the midsubstance for the length of the Achilles tendon until reaching the gastrocnemius. The rope can then be sutured to the Achilles tendon near the site of where the Achilles tendon and the gastrocnemius attach to each other.

Midsubstance Threading

In an embodiment, a placental tissue streamer is threaded through the midsubstance of a tissue post-repair, where the injury is repaired before the streamer is threaded through the tissue. For example, in a tendon rupture, the tendon can be sutured together at the rupture site. Then a placental tissue streamer threaded through the midsubstance of the repaired tendon and attached to both ends of the tendon near the tendon's natural attachment site.

In an embodiment, a placental tissue streamer is threaded through the midsubstance of a tissue; however, the streamer is not completely covered by the tissue. In such an embodiment, the streamer exits the midsubstance and outer layer of the tissue, becoming exposed to the environment in the patient cavity.

In an embodiment, a placental tissue streamer is located adjacent to the repaired tissue. In such an embodiment, one end of the streamer is attached at a placental tissue streamer attachment site and the other end of the streamer is attached at a second placental tissue streamer attachment site in such a way that the streamer spans the tissue at the site of repair.

Wrapping

A graft (e.g., allograft, autograft, xenograft, engineered tissue scaffold) or tissue (e.g., a tissue to be treated) can be wrapped with one or more placental tissue streamers, engineered scaffold placental tissue hybrids, suture placental tissue hybrids, collagen membrane, or placental tissue patch hybrids. The placental tissue streamers, engineered scaffold placental tissue hybrids, suture placental tissue hybrids, collagen membrane, or placental tissue patch hybrids can be, for example, anchored to themselves, to the graft, to the tissue to be treated, to tissue adjacent or surrounding the tissue to be treated, or to one or more attachment sites. A placental tissue streamer, engineered scaffold placental tissue hybrid, suture placental tissue hybrid, collagen membrane, or placental tissue patch hybrid can be wrapped around a graft or tissue such that the graft or tissue is substantially covered by the streamer or hybrid. In an embodiment, 50, 60, 70, 80, 90, 95, 98, 99 or 100% (or any range between about 50% and 100%) of the surface of the graft or tissue is covered by the wrapped placental tissue streamer or hybrid. In an embodiment, all of the graft or tissue is covered by the wrapped placental tissue streamer, engineered scaffold placental tissue hybrid, suture placental tissue hybrid, collagen membrane, or placental tissue patch hybrid except for the ends of the graft or tissue. In an embodiment the placental tissue steamer, engineered scaffold placental tissue hybrid, suture placental tissue hybrid, or placental tissue patch hybrid is of a width that is sufficient for the desired coverage of the graft or tissue and is wrapped one or more times around the graft or tissue. In an embodiment, the placental tissue steamer, engineered scaffold placental tissue hybrid, suture placental tissue hybrid, collagen membrane, or placental tissue patch hybrid is not as wide as the length of the graft or tissue and is wrapped around the graft or tissue so that that longitudinal edges (long edges) of the placental tissue steamer, engineered scaffold placental tissue hybrid, suture placental tissue hybrid, collagen membrane, or placental tissue patch hybrid overlap to confer full coverage of the graft or tissue. The latitudinal edges (short edges) of the placental tissue steamer, engineered scaffold placental tissue hybrid, suture placental tissue hybrid, collagen membrane, or placental tissue patch hybrid can be anchored either to the graft or tissue itself or to one or more attachment sites.

Prior to wrapping the graft or tissue with one or more the placental tissue steamers, engineered scaffold placental tissue hybrids, suture placental tissue hybrids, collagen membranes, or placental tissue patch hybrids, the graft or tissue can be contacted with one or more biological agents, such as platelet rich plasma (PRP), bone marrow concentrate (BMC), adipose derived growth factors, viscous amnion, amniotic epithelial cells (AE) cells, stem cells, growth factors (e.g., epidermal growth factor (EGF), platelet-derived growth factor (PDGF), vascular endothelial growth factor (VEGF), angiogenin, transforming growth factor-β2 (TGF-β2), and tissue inhibitors of metalloproteinases (e.g., TIMP-1 and TIMP-2)), adipose derived growth factors, umbilical cord-derived cells (UCD) cells, chorionic trophoblasts (CT), amnion derived or chorion derived mesenchymal stromal cells, or combinations thereof. Biological agents are any agents that provide enhanced healing, regeneration, and improved graft incorporation. One or more of the biological agents (e.g., PRP or BMC) can be obtained from the patient to be treated.

In an embodiment, a placental tissue steamer, engineered scaffold placental tissue hybrid, suture placental tissue hybrid, or placental tissue patch hybrid is wrapped around the tissue or graft such that one or more pockets or spaces are created between the tissue or graft and the placental tissue streamer or hybrid. One or more biological agents can be injected or otherwise provided to the one or more pockets or spaces.

In one embodiment, at the completion of ACL graft preparation, a graft can be wrapped in placental tissue (e.g., amnion, chorion, or umbilical cord) or a placental tissue streamer hybrid or collagen membrane. One, two, or more sutures can connect the graft to the placental tissue or placental tissue streamer hybrid wrap at either end or at one end of the graft. The graft can be wrapped multiple times creating multiple layers. One cerclage stitch can be placed at either end of the placental tissue or placental tissue streamer hybrid wrap after wrapping. A running stitch can also be placed at the end of the wrap. The two cerclage stitches and the running stitch can create multiple water-tight compartments (i.e., pockets or spaces) dependent on the number of layers of wrap. The compartments, which can be water-tight, can be filled or contacted with a biological agent after implantation. In an embodiment, the biological agent comprises stem cells that can be injected into a water-tight compartment. In an embodiment, the stem cells are harvested from the patient receiving the ACL graft. The stem cells can be harvested from the distal femur (the same surgical site used for the ACL graft) using a bone marrow aspiration needle and stem cells can be concentrated or purified from the bone marrow aspirate.

Once the graft has been inserted into the joint and secured, the arthroscopic fluid can be evacuated from the joint. The water-tight compartments of the placental tissue streamer wrapped graft can be injected with a biological agent (e.g., platelet rich plasma (PRP); bone marrow concentrate (BMC); viscous amnion; growth factors; stem cells (e.g., AE stem cells), etc.).

An embodiment includes a method of treating musculoskeletal tissue injury or degeneration in a subject. At least one placental tissue streamer, placental tissue patch hybrid, or engineered scaffold placental tissue streamer hybrid is wrapped around a tissue (e.g., damaged, injured, or degenerated tissue, an engineered scaffold, or graft), to form a tissue hybrid. The tissue hybrid is contacted with a musculoskeletal tissue injury or degeneration site in a subject (e.g. a site of damaged, injured, or degenerated tissue) or tissue to be treated. The placental tissue streamer, placental patch hybrid, or engineered scaffold placental tissue streamer hybrid or tissue hybrid can be optionally attached to the subject at, for example, the damaged, injured, or degenerated tissue (i.e., the tissue to be treated) or to healthy tissue adjacent to or surrounding the damaged, injured, or degenerated tissue.

Placental Tissue

Placental tissue contains immunosuppressive cytokines and lacks surface antigens, the combination of which results in a lack of rejection in patients treated with placental tissue. Immunosuppressive cytokines include, but are not limited to, interleukin-4, interleukin-10, and transforming growth factor. Antigens important for the lack of rejection include, but are not limited to, HLA-A, HLA-B, HLA-C, and β2-microglobulin.

Placental tissue can be collected from a female mammal at the time the female mammal is giving birth to offspring. Placentae are usually discarded following child birth. Placental tissue can be collected instead of discarding the entire placenta to medical waste. This collection can take place from a cesarean birth. In an embodiment, collected placental tissue is prepared by removing epithelial cells by gentle mechanical scraping or by other well-known methods. In another embodiment, epithelial cells are not removed from the collected placental tissue.

In an embodiment, placental tissue is biopreserved, meaning the tissue is recovered and prepared so that the integrity and functionality of cells and tissues are able to be held outside their native environment for extended storage times. Biopreservation methods are well known, and such methods are used in the preparation of placental tissue. Such methods include, but are not limited to, hypothermic preservation, chemical preservation, dehydration, lyophilizaton, desiccation, and cryopreservation. Hypothermic preservation is the storage of tissue at lower than room or body temperature but without freezing the tissue. Cryopreservation is the preservation of tissue by freezing the tissue and storing at temperatures lower than 0° C. The placental tissue can also be stored through normothermic culture, where the tissue is kept at the temperature of its native environment. As is known in the art, the medium that the tissue is stored in depends upon the method of biopreservation used.

In embodiments where placental tissue is biopreserved, the tissue is reconstituted prior to methods disclosed herein. Biopreserved placental tissue can be reconstituted in a solution such as saline. The solution can comprise a) platelet rich plasma (PRP), b) bone marrow concentrate (BMC), c) growth factors, d) stem cells, e) adipose derived growth factors, f) amniotic epithelial cells (AE) cells, g) umbilical cord-derived cells (UCD) cells, h) chorionic trophoblasts (CT), i) amnion derived or chorion derived mesenchymal stromal cells, j) chemical additives, or h) combinations thereof. In an embodiment, growth factors include epidermal growth factor (EGF), platelet-derived growth factor (PDGF), vascular endothelial growth factor (VEGF), angiogenin, transforming growth factor-$\beta 2$ (TGF-$\beta 2$), and tissue inhibitors of metalloproteinases (e.g., TIMP-1 and TIMP-2). One or more of the biological agents (e.g., PRP or BMC) can be obtained from the patient to be treated.

AE cells as mentioned above can have at least one cell surface marker selected from the group consisting of stage-specific embryonic antigen-3 (SSEA-3), SSEA-4, tumor rejection antigen 1-60 (TRA1-60), and TRA1-81. Similarly, AE cells may have at least one molecular marker selected from the group consisting of octomer-4 (OCT-4), NANOG, sex determining region Y-box 2 (SOX-2), Lefty-A, fibroblast growth factor-4 (FGF-4), REX-1, and teratocarcinoma-derived growth factor 1 (TDGF-1).

In an embodiment, AE cells can be also be administered to a repair or reconstruction in a patient. In an embodiment, a solution comprising AE cells can be administered to a tissue graft, tissue hybrid, or placental streamer ex vivo prior to implantation into a subject. Although AE cells can comprise multipotent cells, the administration of AE cells in clinical settings and to immunodeficient mice (e.g., SCID and Rag-2 knockout mice) have not produced teratomatous growth.

In an embodiment, a method includes preparing PRP and/or BMC from a patient, reconstituting a placental tissue (e.g., amnion or chorion) with the prepared PRP and/or BMC, and augmenting the patient's damaged soft tissue or graft with the placental tissue. In an embodiment, a method includes reconstituting a placental tissue with media comprising AE cells, and augmenting a patient's damaged soft tissue or graft with the placental tissue. In an embodiment, a method includes preparing PRP and/or BMC from a patient; reconstituting placental tissue with the PRP and/or BMC from the patient supplemented with AE cells; and augmenting the patient's damaged soft tissue or graft with the placental tissue. Additionally, a placental tissue streamer or placental tissue hybrid can be injected or attached to the damaged soft tissue or graft's midsubstance in any of the disclosed methods herein.

In an embodiment, placental tissue (e.g., amnion, chorion, or umbilical cord tissue) is decellularized. Tissues can be decellularized using any method of decellularization known in the art. For example, amnion can be decellularized by removing the cell membrane and cellular debris using gentle mechanical disruption methods. These methods disrupt the cellular membrane, while avoiding damaging or disturbing the amnion's complex infra-structure. Gentle mechanical disruption methods include, for example, scraping the surface of the amnion, agitating the amnion, or stirring and washing the amnion in a suitable volume of fluid, e.g., distilled water or saline (e.g., 0.9% saline), for a suitable amount of time (e.g., about 15, 30, 60, 90 minutes or more). The amnion is thereby disrupted and the cellular debris is removed from the amnion. In another embodiment, the amnion, chorion, umbilical cord tissue or placental tissue is not decellularized.

A placental tissue (e.g., a placental streamer) can comprise viable tissue cells native to placental tissue (e.g., amniotic tissue, chorionic tissue, umbilical cord tissue, or combinations thereof), extracellular matrix that is native to placenta (e.g., amniotic tissue, chorionic tissue, umbilical cord tissue, or combinations thereof), or both viable tissue cells native to placental tissue and extracellular matrix that is native to placental tissue. A placental tissue can be amnion or an amnion streamer. Likewise, placental tissue according the embodiments disclosed herein can also comprise non-viable cells.

Engineered Tissue Scaffolds

In an embodiment, an engineered tissue scaffold comprises a structural component and cells attached to the engineered tissue scaffold. In an embodiment, an engineered tissue scaffold is a fully developed tissue that comprises a collection of cells assembled to fulfill a common function. In an embodiment, an engineered tissue scaffold is used in place of a damaged tissue or tissue graft. In an embodiment, an engineered tissue scaffold is used in conjunction with damaged tissue or tissue graft. In an embodiment, an engineered tissue scaffold, damaged tissue, and tissue graft are used in combination. In an embodiment, an engineered tissue scaffold comprises a midsubstance of a tissue where at least one placental tissue streamer is located.

Engineered tissue scaffolds are materials that can be used to encourage desirable cellular interactions and the formation of new functional tissues. One of more types of cells can be 'seeded' into or onto scaffolds. Cells include, for example, bone marrow mesenchymal stem cells (BM-MSCs), umbilical cord-derived mesenchymal stem cells (UC-MSCs), adult or embryonic stem and progenitor cells, induced pluripotent cells, tenocytes, osteoblasts, nerve cells, cardiac cells, myocytes, fibroblasts or combinations thereof.

Engineered tissue scaffolds can be made up of natural or synthetic materials that can be biodegradable or permanent). Examples of these materials used in enaineered tissue scaffolds are polyesters, nylon, polyurethrine, polylactic acid (PLA), polyglycolic acid (PGA), polycaprolactone (PCL), polystyrene, poly-1-lactic acid (PLLA), poly-dl-lactic-co-glycolic acid (PLGA), polyvinyl acetate (PVA), polyvinyl chloride (PVC), polyethylene glycol (PEG), hydrogels, hydrogels comprising PLA, PGA, PCL, polystyrene, PLLLA, PLGA, PVA, PVC, PEG, or combinations thereof, agarose, alginate, hyaluronan, proteins (e.g., silk, collagen, gelatin, fibrinogen, fibrin, elastin, keratin, actin, and myosin), polysaccharidic materials (e.g., cellulose, amylose, dextran, chitin, chitosan and glycosaminoglycans (GAGs), or polynucleotides (DNA, RNA).

In an embodiment an engineered tissue scaffold comprises one or more placental tissue streamers. The combination of an engineered tissue scaffold and one or more placental tissue streamers is an engineered scaffold placental tissue hybrid. The one or more placental tissue streamers can be attached to (by, for example sutures or anchors) or woven into an engineered tissue scaffold to form an engineered scaffold placental tissue hybrid. Optionally, the one or more placental tissue streamers can be held in contact with an engineered tissue scaffold without sutures or anchors to form an engineered scaffold placental tissue hybrid.

An engineered scaffold placental tissue hybrid can be attached to a tissue to be treated or can be attached to healthy tissue adjacent or surrounding to the site of the injury, damage, or weakness. An engineered scaffold placental tissue hybrid can be attached to muscle, tendon, ligament, joint, connective tissue, cartilage, bone, or the like.

An engineered scaffold placental tissue steamer hybrid can be used to treat musculoskeletal tissue injury or degeneration in a subject. One or more engineered tissue scaffolds can be combined with one or more placental tissue streamers to form an engineered scaffold placental tissue steamer hybrid. The engineered scaffold placental tissue steamer hybrid can be contacted with a tissue to be treated (e.g., damaged, injured, or degenerated tissue). The engineered scaffold placental tissue steamer hybrid can optionally be attached to the tissue to be treated or to healthy tissue adjacent to or surrounding the tissue to be treated.

Streamers

In an embodiment, placental tissue is cut into streamers to form placental tissue streamers. In an embodiment, the streamer is any length ranging from about 60 cm to about 1 cm, e.g. about 60, 50, 40, 30, 25, 20, 15, 10, 8, 6, 5, 4, 3, 2, 1, 0.5, 0.1, cm or less. In an embodiment, the streamer is any width from about 20 cm to about 0.5 cm, e.g. about 20, 18, 15, 12, 10, 9, 8, 7, 6, 5, 4, 3, 2, 1, 0.5, 0.1, 0.05, 0.01 cm, or less. A streamer can have a longer length than the width, can be square, or can be any other suitable shape. The streamer can be the full thickness of the amniotic tissue or chorion membrane or portions or layers of amniotic tissue, chorion membrane or umbilical cord. A placental streamer can be comprised of amnion, chorion, umbilical cord tissue, or combinations thereof. In an embodiment, a grouping of streamers is used where "grouping" represents a combination of more than one streamers used together in the same tissue hybrid. In an embodiment, at least two placental tissue streamers (e.g., 2, 3, 4, 5, or more) are entwined together so as to form a placental tissue streamer rope. In an embodiment, at least two placental tissue streamers (e.g., 2, 3, 4, 5, or more) are stacked together so as to form a placental tissue streamer stack. The placental tissue streamers of the ropes of stacks may comprise 1 or more sutures to hold the streamers together.

Placental Tissue Streamer Suture Hybrid

A placental tissue streamer can be surrounded by suture. The combination of a placental tissue streamer surrounded by suture is a placental tissue streamer suture hybrid. In an embodiment, a suture is a tubular sheath defining an empty bore. In an embodiment, the bore of the suture has a diameter of about 2 mm to about 0.4 mm, i.e. about 2.0, 1.8, 1.6, 1.5, 1.4, 1.3, 1.2, 1.1, 1.0, 0.9, 0.8, 0.7, 0.6, 0.5, and 0.4 mm. A suture can be bioabsorbable or non-bioabsorbable. Where a suture is non-bioabsorable, it can provide permanent structural support for the augmentation of tissue healing, or tissue regeneration or both. The suture can be a porous structure or a suture with gaps. That is, the suture surrounding the placental tissue streamer can have pores or gaps in the structure such that the placental tissue streamer is retained within the suture, and such that biological agents or molecules associated with the placental tissue streamer can move out of the suture and into the surrounding tissues. A porous or gapped structure of a suture can allow for a faster delivery of regenerative biomolecules to damaged or healthy tissue. A suture can be comprised of, for example, collagen or combinations of various polymers and collagens or any other suitable material.

One or more placental streamers can be threaded longitudinally through the opening or bore of the suture to form a placental tissue streamer suture hybrid. The placental tissue streamer suture hybrid can then be used to suture damaged, degenerated, injured, or healthy tissue through methods known in the art. A placental tissue streamer suture hybrid supplies a structural augmentation, biological augmentation, and/or support to heal, remodel, and/or regenerate damaged, injured, or healthy tissues.

A placental tissue streamer suture hybrid can have "tails" of additional suture material on their ends. A placental tissue streamer suture hybrid can have a needle or anchor on one end of the suture.

The placental tissue streamer naturally contains regenerative biomolecules important in healing, regeneration, and growth processes. The placental tissue streamer with its regenerative biomolecules inside the suture bore can act as an augmentation boost for the repair of damaged or injured tissue or healthy tissue.

A placental tissue streamer suture hybrid can be used in primary repair of damaged tissues, such as tendon or ligament injury (e.g., rotator cuff repair).

A placental tissue streamer suture hybrid can be used in augmentation of repaired or reconstructed tissue. In an embodiment, a method of surgical repair includes securing a reinforcement construct adjacent to a repaired or replacement ligament or tendon, wherein the reinforcement construct is secured by fixation devices, wherein a first fixation device and the second fixation device are secured adjacent to the repaired or replacement ligament's or tendons' attachment sites (e.g., a ligament's insertion and origin points). In an embodiment, the reinforcement construct can be a placental tissue streamer suture hybrid. A reinforcement construct comprising a placental tissue streamer can be placed adjacent to repaired musculoskeletal tissue to support healing with both the structural support of a hybrid suture and the biological augmentation of the placental membrane.

A placental tissue streamer suture hybrid can be attached to a tissue to be treated or can be attached to healthy tissue adjacent to the site of the injury, damage, or weakness. A placental tissue streamer suture hybrid can be attached to muscle, tendon, ligament, joint, connective tissue, cartilage, bone, or the like.

A placental tissue streamer suture hybrid can be loaded into a suture anchor to form a placental tissue steamer suture hybrid anchor for augmentation of the suture anchor to bone and soft tissue. An example would be a SutureBridge™ soft tissue reattachment or repair technique, which when loaded with the placental suture construct, and loaded within the suture anchor, becomes a biologically enhanced SutureBridge™. SutureBridge™ techniques are used, for example, in Achilles tendon reattachment following debridement. An hourglass pattern of sutures is laid over the distal end of the tendon. A multianchor (e.g., about 2, 3, 4, 5, 6, or more) construct enables a greater area of compression for the Achilles tendon on the calcaneus, improving stability and allowing for earlier return to normal activities.

Placental Tissue Patch Hybrid

A placental tissue patch hybrid comprising placental tissue (e.g., placental tissue streamers) and a mesh construct can be used to deliver difficult or delicate biologic constructs to a surgical repair, reconstruction, or regeneration site and maintain their presence at the site post-operatively. In an embodiment, a placental tissue (e.g., a placental tissue streamer) is interwoven in the mesh construct, is present in a compartment or pocket of the mesh construct, or attached on the top, the bottom, or both the top and bottom of a mesh construct. A mesh construct can be a mesh biologic (i.e., a biomesh), that is comprised of an organic biomaterial such as porcine dermis, porcine small intestine submucosa, bovine dermis or pericardium, and the dermis or fascia lata of a cadaveric human. These materials can be further processed to acellullar, porous extracellular matrix scaffolds of collagen and elastin. Some source growth factors can remain, which attract endothelial cells and subsequent fibroblasts into the mesh. A mesh construct can also be a synthetic mesh.

A mesh construct can be a biocompatible fabric. The fabric can be, for example, polymers of polyethylene, polypropylene, polyester (e.g., polyethylene terephthalate), polyether ether ketone, polyacetal, polyurethane, polytetrafluoroethylene, polycarbonate, polysulfone, polyamide, copolymers thereof, or combinations thereof.

A placental tissue patch hybrid can also include bioresorbable synthetic polymers, such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers.

A placental tissue patch hybrid can be any shape or size and can comprise one or more pieces of placental tissue (e.g., one or more placental tissue streamers). For example the placental tissue patch hybrid can be a strip, rectangular, square, circular, ovoid or cut to any size or shape necessary. In an embodiment, a placental tissue patch hybrid is shaped according to the anatomy for the site of application.

A placental tissue hybrid patch can be adhered or attached to a surgical repair site. A surgical repair site can be a rotator cuff tendon repair or augmentation, an anterior cruciate ligament (ACL) repair, etc. In an embodiment, a partial thickness rotator cuff tear can be treated with a placental tissue hybrid patch. In an embodiment, the patch is attached over the repair site. For example, the patch can be positioned over the repair site and attached to adjacent muscles, ligaments, tendons, and bones. In an embodiment, a patch is attached via at least two flexible strands (e.g., suture, suture tape, or anchoring devices (e.g., FiberTak® anchor) etc.) to the surrounding healthy tissue. In an embodiment, a placental tissue patch hybrid can be positioned over a rotator cuff tendon repair. The shape of the patch can be adapted to the anatomy of the shoulder. Once positioned over the shoulder, the patch can be sutured to the site via flexible strands sutured through the adjacent muscles and/or through suture anchors drilled into adjacent bones.

A placental tissue hybrid patch can be attached to a tissue to be treated, or can be attached to healthy tissue adjacent or surrounding to the site of the injury, damage, or weakness. A placental tissue hybrid patch can be attached to muscle, tendon, ligament, joint, connective tissue, cartilage, bone, or the like.

In another embodiment, a placental tissue patch hybrid can be wrapped around a repaired ligament or other repaired, damaged, or degenerated tissue. For example, a placental tissue patch hybrid can be wrapped around a reattached ligament such as the ACL. The placental tissue patch hybrid can be wrapped so one lateral edge of the patch contacts its opposite lateral edge. In another example, the two opposite lateral edges contact and there is overlap between the two lateral edges, where one lateral edge is on top of the second lateral edge.

In an embodiment a placental tissue patch hybrid is used in meniscal repair, or in the filling of meniscal loss.

In an embodiment, a placental tissue patch hybrid is used in rotator cuff repair. A rotator cuff tendon, for example, a supraspinatus tendon, an infraspinatus tendon, a teres minor tendon, a subscapularis tendon, and/or a long head tendon, can be accessed and optionally debrided to remove any frayed intra-substance tissue from the torn or damaged tendon. The rotator cuff tendon can be pulled back into anatomical position if necessary, and a placental tissue patch hybrid can be secured to the tendon by, for example, sutures or suture anchors. Where the tendon is too short due to for example, degeneration or contracture, a placental tissue patch hybrid can be used as a bridge to span any gap. The placental tissue patch hybrid can be wrapped around the tendon or can be placed over or along the tendon.

In an embodiment the top portion of the humerus can be decorticated. This can enhance biological incorporation and help with reattachment of the tendon. The tendon, the placental tissue patch hybrid, or both the tendon and placental tissue patch hybrid can be attached to the humerus by, for example, screws, suture anchors, adhesives, and the like.

The placental tissue patch hybrid can comprise one or more pockets or compartments. One or more biological agents can be placed into the one or more pockets or compartments. In an embodiment the placental tissue patch hybrid can be wrapped around a tendon leaving one or more pockets or compartments between the placental tissue patch hybrid and the tendon. One or more biological agents can be placed into the one or more pockets or compartments after the placental tissue patch hybrid is wrapped around the tendon.

In an embodiment, a placental tissue patch hybrid as disclosed herein can be soaked in a solution comprising a biological agent such as: a) platelet rich plasma (PRP), b) bone marrow concentrate (BMC), c) growth factors, d) stem cells, e) adipose derived growth factors, f) amniotic epithelial cells (AE) cells, g) umbilical cord-derived cells (UCD) cells, h) chorionic trophoblasts (CT), i) amnion derived or chorion derived mesenchymal stromal cells, or j) combinations thereof prior to implantation. One or more of the biological agents (e.g., PRP or BMC) can be obtained from the patient to be treated. In an embodiment, a soaked placental tissue patch hybrid can be applied to a surgical repair site, wherein a tendon, ligament, muscle, bone, or a combination thereof is repaired. A soaked placental tissue patch hybrid can be applied to damaged, injured, or degenerated tissue or any other tissue to be treated.

Patch Pockets and Contents of Pocket

In another embodiment, a placental tissue hybrid patch comprises one or more compartments or pockets. The compartments can occur along the entire aspect of the placental tissue patch hybrid, especially the edges where incorporation with native tissues can be important. In an embodiment, the compartments can be aligned in rows over the entire mesh construct or over only a part of the mesh construct. The compartments can be any shape or size, for example, a strip, rectangular, square, circular, ovoid or any size or shape necessary. A compartment can be porous to allow the contents to migrate out of the compartment or to allow the contents contact with the tissue and/or the treatment site.

A compartment can be made in a mesh construct by sewing, securing, or folding the mesh construct so that one or more compartments are available.

The compartment(s) are capable of containing a placental tissue (e.g., a placental streamer) and/or a biological agent, which can migrate from the patch to the repair site over time. One or more of the biological agents (e.g., PRP or BMC) can be obtained from the patient to be treated. In a further embodiment, a placental tissue patch hybrid comprises a placental tissue interwoven within a mesh construct and includes one or more compartments capable of containing a biological agent.

Patch/Wrap Uses

Placental tissue patch hybrid compositions can be used to replace tissue loss, such as in the case of massive irreparable rotator cuff tears, patellar tendon tears with tissue loss, or unreconstructable tissue loss of ligament, meniscus, glenoid or acetabular labrum. In such an embodiment, the mesh construct includes initial structural scaffolding and strength, while the placental tissue and/or biological agent provide biologic stimulus for the ingrowth, regeneration, and reformation of damaged or absent musculoskeletal tissues. A specific example includes a superior capsular reconstruction procedure using a placental tissue patch hybrid composition instead of an allograft or xenograft tissue.

Placental tissue patch hybrid compositions can be used to augment damaged musculoskeletal tissues. Specific examples include non-structural partial thickness rotator cuff tears, meniscal tears or loss, and patellar tendon rupture. In such cases the mesh construct supplies mechanical strength while the placental tissue and/or biological agent supplies biological healing augmentation to the injured or degenerative tissue.

In an embodiment, a placental tissue patch hybrid can be used to augment biologic healing in the absence of structural repair. An example would be a partial thickness rotator cuff tear, which does not require structural repair. The placental tissue patch hybrid, optionally comprising a biological agent, can be placed over the damaged portion of the tendon and secured in place, allowing the elution and migration of factors from the placental tissue or biological agents to be delivered to the site with added structural support. This can improve healing times or allow for faster rehabilitation programs.

A tissue hybrid can be used to repair, reconstruct, or regenerate tissue in a subject. The tissue hybrid can be a tissue with a midsubstance at least one placental tissue streamer, wherein the placental tissue streamer is located through the midsubstance or periphery of the tissue hybrid. A tissue hybrid can also be an engineered tissue placental tissue hybrid, a suture placental tissue hybrid, or a placental tissue patch hybrid. The injury or degeneration to the subject can comprise damaged musculoskeletal tissue, and the repair or augmentation can comprise rejoining the damaged musculoskeletal tissue and at least one placental tissue streamer to bone, tendon, ligament, connective tissue, cartilage, joint, or muscle of the subject.

In repairs or regeneration not requiring rejoining, the streamer, engineered tissue placental tissue hybrid, suture placental tissue hybrid, or placental tissue patch hybrid can be placed along or within the damaged tissue to augment healing, repair, reconstruction, or regeneration.

Kits

Compositions include kits comprising one or more of placental tissue streamers, placental tissue, engineered scaffold placental tissue hybrid, suture placental tissue hybrid, placental tissue patch hybrids, or tissue hybrids. Kits can be self-contained, single use, and readily available, which will provide some or all of the necessary materials for the efficient use and delivery of the placental tissue, streamers, and tissue hybrids including, for example, buffers, biological agents, engineered tissue scaffolds, sutures, anchors, insertion devices, or needles. In an embodiment, a kit includes all of the necessary materials for the efficient use and delivery of the placental tissue, streamers, and tissue hybrids including, for example, buffers, biological agents, engineered tissue scaffolds, sutures, anchors, insertion devices, or needles, but does not include the placental tissue, streamers, or tissue hybrids A kit can be, for example, designed for intraoperative delivery of a placental tissue streamer directly into damaged or injured tissues, such as a partial thickness rotator cuff tear or lateral epicondylitis degeneration of the extensor carpi radialis brevis. Such a kit can contain, for example, one or more placental tissue streamers (e.g., about 0.5 cm×8 cm), a straight or curved suture lasso, a notched nitinol "plunger", and one or more (e.g., 2, 4, 6) 4-0 LONG fiberloops.

In another example, a kit can be designed for delivery of a placental tissue patch hybrid. Such a kit could contain a mesh patch (engineered tissue scaffold) 5 cm×5 cm rectangular or custom shaped placental patch, 1×8 cm, a red fiberstick tube (beveled on leading end, split on trailing end), a long (20 cm) nitinol loop, and (2) 4-0 LONG fiberloops and nitinol slotted inserter.

In another example, a kit can contain one or more components necessary for delivery of a placental tissue streamer suture hybrid. These kits can be available in several sizes depending on the size of desired suture and the placental tissue streamer suture hybrid can be independently inserted or loaded into a suture anchor. In an example, a kit can contain one or more of placental tissue streamers (e.g., about 1 cm×8 cm), 357 double tailed suture tube (e.g., about 8 cm long tube and about 10 cm long tails), a thin plastic tube beveled on leading end and split on trailing end, a nitinol loop (e.g., about 20 cm long), 4-0 long FiberLoops® (continuous loop of a suture such as FiberWire® (e.g., a multi-strand long chain ultra-high molecular weight (UHMWEP) core with a braided jacket of polyester and UHMWEP), and multiple needle options. The plastic tube can be preloaded into the 357 double tailed suture tube.

A surgeon provided with a kit need only to cut the placental tissue streamer, place a luggage tag suture through the placental tissue streamer, and load the placental tissue streamer into the nitinol wire, or deliver the placental tissue streamer via loading onto a slotted nitinol inserter.

In an embodiment, a placental tissue streamer suture hybrid kit can be used for direct injection/insertion of a placental tissue streamer suture hybrid under ultrasound guidance. A kit can contain, for example, one or more of placental tissue streamer (e.g., about 0.25 cm×8 cm), 14G needle or other sized needle (about 8 cm long), a notched plunger that can fixate the placental tissue streamer, that can be loaded into a needle, and that can be held in place as needle is retracted Definitions Unless defined otherwise, all technical and scientific terms used herein have the same meaning as commonly understood to one of ordinary skill in the art. As used herein, the singular forms "a," "an," and "the" include plural referents unless the context clearly dictates otherwise. For example, reference to a "tissue" means one or more tissues. Further it can include native biologic structure, autograft, allograft, xenograft, and engineered tissue scaffolds.

The terms "or" and "and/or" describe multiple components in combination or exclusive of one another. For example, "x, y, and/or z" can refer to "x" alone, "y" alone, "z" alone, "x, y, and z," "(x and y) or z," "x or (y and z)," or "x or y or z."

"Tissue hybrid" is a tissue comprising at least one placental tissue streamer running through the midsubstance of the tissue, along the edge of the tissue, or wrapped around the tissue. Examples of the tissue in the tissue hybrid include, but are not limited to, muscle, tendon, ligament, cartilage, meniscus, intervertebral disk material, and other connective tissues. The tissue of the tissue hybrid can comprise an "outer layer" and a "midsubstance." In an embodiment, the outer layer and the midsubstance can be made of the same type of tissue. In an embodiment, the outer layer and the midsubstance of the tissue can be made of differing tissue types. After attachment to the patient, the outer layer acts as a covering to the midsubstance, separating the midsubstance from the environment in the patient cavity. The "midsubstance" of the tissue is comprised of a number of cells which make up the raw material of the tissue. An example of an outer layer is the epimysium of a muscle while the muscle is an example of the midsubstance. Another example of an outer layer is the sheath of a tendon while the tendon is an example of the midsubstance. The midsubstance comprises a "midpoint," which is substantially the intermediate or longitudinally central portion of the midsubstance. Neither the midsubstance nor the midpoint has to be the exact center of the tissue. A tissue hybrid also comprises an engineered scaffold placental tissue hybrid in contact with damaged, injured, or degenerated tissue or in contact with a graft tissue. A tissue hybrid also comprises a placental tissue in contact with damaged, injured, or degenerated tissue or in contact with a graft tissue. A tissue hybrid also comprises suture placental tissue hybrid in contact with damaged, injured, or degenerated tissue or in contact with a graft tissue. A tissue hybrid also comprises placental tissue patch hybrid in contact with damaged, injured, or degenerated tissue or in contact with a graft tissue.

"Placental tissue" is tissue that is removed or separated from the placenta. This includes amniotic tissue, chorionic tissue, and umbilical cord tissue.

"Treatment," "treating," "repair," "repairing," "augmentation," and "augmenting" refer to the process of administering or applying a placental tissue to a patient at the site of a musculoskeletal tissue wound, weakness, or injury (i.e., a tissue to be treated) through methods disclosed herein.

"Musculoskeletal tissue injury" or "musculoskeletal tissue injuries" refer to injuries, damage, wear, aging, deterioration, or wounds occurring to the soft tissue of the musculoskeletal system. Examples of musculoskeletal tissues include, but are not limited to, muscle, tendon, ligament, cartilage, meniscus, intervertebral disk, and other connective tissue. Examples of musculoskeletal tissue injuries include, but are not limited to, connective tissue injury, cartilaginous tissue injury, fibrous tissue injury, muscle tissue injury, and skeletal tissue injury such as sprains, strains, tears, partial tears, ruptures, and partial ruptures as well as degenerative tendinopathies, and cartilage wear of soft tissues of the musculoskeletal system. Some specific examples of common musculoskeletal injuries include, but are not limited to, tendinitis, partial thickness tears, tendinopathy, anterior cruciate ligament rupture, Achilles tendon rupture or tendinopathy, rotator cuff tear or tendinopathy, lateral epicondylitis, hamstring tear or strain, calf strains or tearing, bicep tendon rupture, meniscal tearing, medial meniscal degeneration, degenerative disk disease, and "shoulder separation" where the acromioclavicular (AC) joint is separated due to tears in the AC ligament and/or the coracoclavicular ligament.

"Subject" and "patient" are used interchangeably herein and refer to both human and nonhuman animals. The term "nonhuman animals" of the disclosure includes all mammals, e.g., such as nonhuman primates, sheep, dog, cat, horse, cow, and the like.

"Amnion" and "amniotic tissue" are used interchangeably. Amnion is a thin, cellular, extra-embryonic membrane that forms the inner membrane of a closed sac surrounding and protecting a mammalian embryo. Typically, the amnion is a tough, transparent, nerve-free, and nonvascular membrane consisting of two layers of cells, an inner, single-cell layer of ectodermal epithelium and an outer covering of mesodermal, connective and specialized smooth muscular tissue. After birth, the placenta is expelled and the amnion can be seen as a white fringe lining of the inner cavity of the placenta. The amnion can be separated from the placenta. The amniotic tissue is the lining of the fetal environment during gestation and separates the developing fetus from the mother in utero. Amniotic tissue is composed of a number of layers and easily splits into an amnion layer and chorion layer, where the two layers are separated by a layer of Wharton's Jelly, a gelatinous-like intermediate substance. The amnion layer is located on the fetal side of the membrane and is principally composed of three types of material: collagen and extracellular matrix; viable tissue cells and cellular material; and regenerative molecules and growth factors. The collagen and extracellular matrix materials of the amniotic tissue form the structural component providing the tensile strength to the amniotic tissue. The cellular material includes epithelial lining of the amnion facing the developing fetus, but also pluripotent stem cells important in regenerating new cellular materials within the membrane lining. Viable tissue cells present in the amniotic tissue include epithelial stem cells and fibroblasts among others. Epithelial stem cells are native to the amniotic membrane and are biologically active in the healing process. Fibroblasts are also present and provide lining and strengthening of tissues. Regenerative biomolecules important in healing and growth processes are concentrated in the amniotic membrane. Such biomolecules include, but are not limited to, epidermal growth factor, transforming growth factor beta, fibroblast growth factors, platelet-derived growth factors, metalloproteinases, and tissue inhibitor of metalloproteinases.

"Chorion," "chorionic tissue," and "chorionic membrane" refer to tissue that exists during pregnancy between the fetus and mother, which combines with the amnion to form the amniotic sac. Chorion is formed by extraembryonic mesoderm and consists of two layers, an outer layer formed by trophoblast, and an inner layer formed by somatic mesoderm. Chorion is used herein to refer to the outer trophoblast layer, the inner somatic mesoderm layer, or both layers together.

"Umbilical cord tissue" refers to the tissue removed from the umbilical cord, a structure which connects the fetus to the placenta and develops from the yolk sac and allantois of the early fetus. The umbilical cord comprises an outer connective tissue layer, blood vessels (at least one vein and at least one artery), and wharton's jelly. In an embodiment, the blood vessels are removed from the umbilical cord's outer connective tissue layer. In an embodiment, all parts of the umbilical cord are harvested and used, including the blood vessels.

"Streamer" of placental tissue refers to a strip of placental tissue. The strip of placental tissue comprises amniotic membrane tissue, chorion membrane tissue, umbilical cord tissue, and combinations thereof. "Streamer," "strip," "band," and "strand" can be used interchangeably. A streamer is any length ranging from about 60 cm to about 1 cm, e.g. about 60, 50, 40, 30, 25, 20, 15, 10, 8, 6, 5, 4, 3, 2, 1 cm or less. The streamer is any width from about 20 cm to about 0.5 cm, e.g. about 20, 18, 15, 12, 10, 9, 8, 7, 6, 5, 4, 3, 2, 1, 0.5 cm or less. The streamer can be the full thickness of the placental tissue, amniotic tissue, chorion tissue, or umbilical cord tissue. As used herein, "a grouping of streamers" is used where "grouping" represents a combination of two or more streamers used together in the same tissue hybrid.

A "placental tissue streamer rope" is at least two placental tissue streamers (e.g., 2, 3, 4, 5, or more) that are entwined together so as to form a rope-like composition. A placental tissue streamer rope can comprise 1 or more sutures to hold the streamers together in the rope-like form.

A "placental tissue streamer stack" is at least two placental tissue streamers (e.g., 2, 3, 4, 5, or more) that are stacked together so as to form a stack-like composition. The placental tissue streamer stack can comprise 1 or more sutures to hold the streamers together in the stack-like form.

"Placental tissue streamer attachment site" refers to the location of where the placenta tissue streamer is to be attached. The placental tissue streamer attachment site can be in a tissue hybrid, or can be located in healthy tissue adjacent to the site of the injury, damage, or weakness. A placental tissue streamer attachment site can be located in muscle, tendon, ligament, joint, connective tissue, cartilage, bone, or the like. In an embodiment, the placental tissue streamer attachment site is located outside of the tissue hybrid in healthy tissue adjacent to the site of the injury, weakness, or damage.

"Tissue attachment site" refers to the location where tissue is attached. The tissue attachment site may be the same as the placental tissue streamer attachment site; however, the tissue attachment site may be a different site than the placental tissue streamer attachment site. For example, in a repair of a partially ruptured Achilles tendon, the placental tissue streamer can be attached in two places, at the calcaneus and the gastrocnemius, so there are two placental tissue streamer attachment sites. The Achilles tendon can be sutured back to itself at the site of injury, closing the gap left by the tear. Where the Achilles tendon was sutured back together is the tissue attachment site.

A "placental tissue patch hybrid" comprises placental tissue and a mesh construct. The placental tissue can be interwoven in the mesh construct, can be present in a compartment or pocket of the mesh construct, or can be attached on the top, the bottom, or both the top and bottom of a mesh construct. A mesh construct can be a mesh biologic (i.e., a biomesh) or a synthetic mesh.

A "placental tissue streamer suture hybrid" is a placental tissue streamer surrounded by a bioabsorbable or non-bioabsorbable suture. The suture can be a tubular sheath defining a bore wherein a placental tissue streamer is threaded through the bore.

"Autograft" refers to a tissue obtained from the patient's body and that tissue is placed back into the same patient's body. "Allograft" refers to a body tissue obtained from one patient and grafted to a genetically dissimilar patient of the same species. Allograft materials can be obtained from mammalian sources, including, but not limited to, equine, canine, feline, bovine, porcine, sheep, or goat, and human sources. "Xenograft" refers to a tissue or organ obtained from one species and placed into an individual of another species. "Engineered tissue scaffold" refers to a material created to provide structural support for cell attachment and subsequent tissue development.

"Biopreserved tissue" refers to tissue that has been recovered and treated as to keep the integrity and functionality of cells, tissues, and organs held outside of their native environment for extended storage times.

"Pre-repair," "pre-augmentation," "post-repair," and "post-augmentation" refer to the timing of when the placental tissue streamers are threaded through tissue. "Pre-repair" and "pre-augmentation" refer to threading the placental tissue streamer through the midsubstance of the tissue before a damaged tissue is repaired. This also includes using a tissue graft and threading the placental tissue streamer through the midsubstance of the tissue graft before attaching the tissue graft in the subject. "Post-repair" refers to the damaged tissue being repaired or augmented before the threading of the placental tissue streamers. For example, an Achilles tendon can be repaired or augmented through methods known in the art, and then at least one placental tissue streamer is threaded through the repaired Achilles tendon.

"Tissue regeneration" is the renewal and growth of tissues through, for example, proliferation of cells.

"Tissue repair" is the restoration of tissue architecture and function after injury or disease.

"Tissue reconstruction" is the use of allograft tissues, autograft tissues, xenograft tissue, or engineered tissue scaffolds to reinforce and repair tissue.

"Tissue composition" refers to a composition of resident cells prepared from a patient's own tissue (e.g., ligament or tendon). The patient's tissue can be resected and then processed to recover viable cells. A "ligament composition" refers specifically to resident cells prepared from a patient's own ligament that was resected and processed.

EXAMPLES

The examples that follow are illustrative of specific methods and devices disclosed herein and various uses thereof. They are set forth for explanatory purposes only, and are not to be taken as limiting.

Example 1

Rotator Cuff Repair

One exemplary method was the repair of a rotator cuff of a human cadaver. A full thickness tear to the supraspinatus tendon of the rotator cuff was created to mimic a natural tear. The tear was then repaired by placing an amniotic streamer in the midsubstance of the supraspinatus tendon and running into the supraspinatus tissue. The streamer was attached to the supraspinatus muscle at one end and to the head of the humerous at the other. The supraspinatus tendon was then sutured through methods known in the art.

Example 2

Ex-Vivo Amnion Wrapping Procedure

An anterior cruciate ligament graft was prepared for insertion into a joint. It should be noted that this methodology can also be used in soft tissue grafts also (e.g., hamstring grafts). An allograft patellar tendon was wrapped in an amnion membrane. Two sutures were used to connect the graft to the amnion membrane at either end at one end of the graft. The graft was wrapped in amnion multiple times creating multiple layers. One cerclage stitch was placed at either end of the amnion membrane after wrapping. A running stitch was also placed at the end of the amnion membrane. The two cerclage stitches and the running stitch created multiple water-tight compartments (cells), which can be dependent on the number of layers of wrapping. The water-tight compartments were filled with a biological agent after implantation of the graft.

In Vivo Biologic Injection

After the graft was inserted into the joint and secured, the arthroscopic fluid was evacuated from the joint. The graft has water-tight compartments of the amnion wrapped graft. Whole blood was injected into the water-tight compartments of the graft to test biological fluid retention in the joint.

Having described the methods and devices in detail and by reference to specific examples thereof, it will be apparent that modifications and variations are possible without departing from the scope of the methods and devices defined in the appended claims. More specifically, although some aspects of the methods and devices are identified herein as particularly advantageous, it is contemplated that the methods and compositions are not limited to these particular aspects.

What is claimed is:

1. A method of anterior cruciate ligament repair comprising:

a) wrapping amnion tissue around a tissue graft to form a wrapped graft;

b) placing at least one cerclage stitch at either end of the amnion tissue and one running stitch at the end of the wrapped graft to form a water-tight compartment;

c) inserting the wrapped graft into a knee joint; and d) adding i) a ligament composition ii) platelet rich plasma (PRP), bone marrow concentrate (BMC), or a combination of PRP and BMC, and iii) thrombin or an animal source activating agent to cause gelation to the water-tight compartment between the amnion tissue and the tissue graft.

2. The method of claim 1, wherein the amnion is wrapped more than once around the tissue graft.

3. The method of claim 1, wherein the ligament composition and the PRP, BMC, or a combination of PRP and BMC are added to the water-tight compartment as one mixture.

4. The method of claim 1, wherein the ligament composition and the PRP, BMC, or a combination of PRP and BMC are added to the water-tight compartment separately.

5. A method of ligament repair comprising:

a) wrapping placental tissue around a tissue graft to form a wrapped graft;

b) placing at least one stitch at either end of the placental tissue and one stitch at the end of the wrapped graft to form at least one water-tight compartment; and c) adding i) a tissue composition ii) a biological agent and iii) thrombin or an animal source activating agent to cause gelation to the at least one water-tight compartment.

6. The method of claim 5, wherein the at least one water-tight compartment is between the placental tissue and the tissue graft.

7. The method of claim 5, wherein the biological agent is platelet rich plasma, bone marrow concentrate, viscous amnion, a growth factor, or stem cells.

8. The method of claim 5, wherein the placental tissue is wrapped around the tissue graft more than once.

9. The method of claim 8, wherein the biological agent is added to a compartment between different layers of the placental tissue.

10. The method of claim 5, wherein the placental tissue is amnion, chorion, or umbilical cord.

11. The method of claim 5, wherein the placental tissue is a placental tissue streamer, an engineered scaffold placental tissue hybrid, or a suture placental tissue hybrid.

12. The method of claim 5, further comprising inserting the wrapped graft into a knee joint before adding the biological agent to the at least one water-tight compartment.

13. The method of claim 5, further comprising inserting the wrapped graft into a knee joint after adding the biological agent to the at least one water-tight compartment.

14. The method of claim 5, wherein the stitch at the end of the wrapped graft is a running stitch.

15. The method of claim 5, wherein the stitches at either end of the placental tissue are cerclage stitches.

16. The method of claim 5, wherein the tissue graft is a tissue hybrid.

17. The method of claim 5, where in the tissue graft is a patellar tendon, a hamstring graft, or a quadriceps tendon graft.

18. The method of claim 5, wherein the tissue composition and the biological agent are added to the water-tight compartment as one mixture.

19. The method of claim 5, the tissue composition and the biological agent are added to the water-tight compartment separately.

20. The method of claim 5, wherein the tissue composition is particulated, minced, digested, or chopped tissue.

* * * * *